(12) United States Patent
Hu et al.

(10) Patent No.: US 11,690,513 B2
(45) Date of Patent: Jul. 4, 2023

(54) METHODS AND SYSTEM FOR MULTI-CHANNEL BIO-OPTICAL SENSING

(71) Applicant: Massachusetts Institute of Technology, Cambridge, MA (US)

(72) Inventors: Juejun Hu, Newton, MA (US); Tian Gu, Faifax, VA (US)

(73) Assignee: Massachusetts Institute of Technology, Cambridge, MA (US)

( * ) Notice: Subject to any disclaimer, the term of this patent is extended or adjusted under 35 U.S.C. 154(b) by 839 days.

(21) Appl. No.: 16/481,710

(22) PCT Filed: Feb. 13, 2018

(86) PCT No.: PCT/US2018/017906
§ 371 (c)(1),
(2) Date: Jul. 29, 2019

(87) PCT Pub. No.: WO2018/148701
PCT Pub. Date: Aug. 16, 2018

(65) Prior Publication Data
US 2019/0387972 A1 Dec. 26, 2019

Related U.S. Application Data

(60) Provisional application No. 62/458,318, filed on Feb. 13, 2017.

(51) Int. Cl.
*A61B 5/00* (2006.01)
*A61B 5/024* (2006.01)
(Continued)

(52) U.S. Cl.
CPC ........ *A61B 5/0059* (2013.01); *A61B 5/02416* (2013.01); *A61B 5/0816* (2013.01);
(Continued)

(58) Field of Classification Search
CPC ...... A61B 2562/0238; A61B 2562/043; A61B 2562/046; A61B 5/0059; A61B 5/02416;
(Continued)

(56) References Cited

U.S. PATENT DOCUMENTS

| | | |
|---|---|---|
| 5,596,986 A | 1/1997 | Goldfarb |
| 5,774,213 A | 6/1998 | Trebino et al. |

(Continued)

OTHER PUBLICATIONS

ISA/US, International Search Report and Written Opinion for PCT application No. PCT/US2018/017906 dated May 2, 2018, 20 pages.

*Primary Examiner* — Yi-Shan Yang
*Assistant Examiner* — Alexei Bykhovski
(74) *Attorney, Agent, or Firm* — Daly, Crowley, Mofford & Durkee LLP

(57) ABSTRACT

A sensor, such as a photoplethysmography sensor, for non-invasively monitoring a characteristic of an organism, such as a vital body sign. The sensor has multiple light sources disposed on a substrate and an array of optical probing channels for conveying light from the light sources to a probed region. Each detector pixel of an array of detector pixels receives light from a respective optical detection channel after interaction with a subregion of the probed region and spatial filtering, and generates a corresponding pixel signal. A processor derives a value of the vital body sign based at least upon the plurality of pixel signals

20 Claims, 10 Drawing Sheets

(51) Int. Cl.
  *A61B 5/08* (2006.01)
  *A61B 5/1455* (2006.01)
(52) U.S. Cl.
  CPC ... *A61B 5/14551* (2013.01); *A61B 2562/0238* (2013.01); *A61B 2562/043* (2013.01)
(58) Field of Classification Search
  CPC ............ A61B 5/02427; A61B 5/02438; A61B 5/0261; A61B 5/0816; A61B 5/1075; A61B 5/1079; A61B 5/14551; A61B 5/14552; A61B 5/489; A61B 5/6824; A61B 5/6826; A61B 5/7214
  See application file for complete search history.

(56) References Cited

U.S. PATENT DOCUMENTS

| | | | |
|---|---|---|---|
| 5,817,008 | A | 10/1998 | Rafert et al. |
| 6,031,603 | A | 2/2000 | Fine et al. |
| 2003/0007124 | A1* | 1/2003 | Levine .................... A61F 9/008 351/206 |
| 2011/0082355 | A1 | 4/2011 | Eisen et al. |
| 2011/0144462 | A1 | 6/2011 | Lifsitz et al. |
| 2014/0171759 | A1* | 6/2014 | White .................. A61B 5/6835 600/306 |
| 2014/0343383 | A1 | 11/2014 | Sato |
| 2015/0044098 | A1 | 2/2015 | Smart et al. |
| 2016/0003613 | A1* | 1/2016 | Atiya ................. A61B 1/00009 356/612 |
| 2016/0069743 | A1 | 3/2016 | McQuilkin et al. |
| 2016/0097716 | A1* | 4/2016 | Gulati .................. A61B 5/1495 250/340 |
| 2016/0270656 | A1* | 9/2016 | Samec ................. A61B 3/0025 |
| 2018/0078155 | A1* | 3/2018 | Baek ....................... A61B 5/742 |
| 2018/0296103 | A1* | 10/2018 | Rege .................... A61B 5/7207 |

* cited by examiner

METHODS AND SYSTEM FOR MULTI-CHANNEL BIO-OPTICAL SENSING

CROSS-REFERENCE TO RELATED APPLICATIONS

This application is the national phase entry of International Patent Application No. PCT/US2018/017906 filed Feb. 13, 2018, which claims the priority of U.S. Provisional Application No. 62/458,318, filed Feb. 13, 2017, the disclosures of which are hereby incorporated by reference in their entirety.

TECHNICAL FIELD

The present invention relates to the optical monitoring of characteristic of an organism, such as a vital body sign, and, more particularly, to photoplethysmographs and speckle imaging incorporating arrays of optical channels that collectively guide light to a plurality of loci within a biological tissue of interest.

BACKGROUND ART

By sensing the interaction between light and blood vessels, photoplethysmographic (PPG) measurements allow non-invasive optical monitoring of vital body signs such as blood oxygen saturation, heart rate, blood flow rate, etc. PPG sensors have been widely used in clinical cardiovascular monitoring systems, such as pulse oximeters, respiration monitors, blood flowmeters, cardiac output monitors, blood pressure systems, detection of cardiac arrhythmia, sleep disorder monitors, peripheral vascular disease assessment, etc. Wearable biosensors for non-invasive continuous cardiovascular monitoring are valuable for real-time physiological monitoring, such as of patients in the hospital, athletes in training, soldiers on combat missions, astronauts in space, etc., as well as for long-term disease prevention and health promotion. A review of applications may be found in Allen, "*Photoplethysmography and its application in clinical physiological measurement,*" *Physiol. Meas.*, vol. 28, pp. R1-R39, (2007), which is incorporated herein by reference.

However, wearable PPG sensors (e.g., commercial heart rate monitors) are far from exhibiting performance characteristics that would allow them to become reliable for mobile applications. They are prone to motion artifacts, low signal-to-noise ratio (SNR), and undesirable form factor, probing site restrictions, and excessive power consumption.

Conventional PPG pulse oximeters illuminate a part of the skin with a pair of light emitting diodes (LED) and measure transmitted or reflected light using a photodetector (PD). Basic principles of PPG pulse oximetry include measurement of absorption spectra of oxygenated hemoglobin ($HbO_2$) and deoxygenated hemoglobin (Hb) in blood vessels and optical detection of periodic blood volume variations caused by heart pulsation, as described in Mendelson, "Pulse oximetry: theory and applications for noninvasive monitoring," *Clin. Chem.*, vol. 38, pp. 1601-7, (1992), incorporated herein by reference. The two common forms of molecules in blood, oxygenated hemoglobin and deoxygenated hemoglobin, have distinct optical absorption properties in the wavelength band between 500 nm and 1000 nm, with absorption of Hb (10) and $HbO_2$ (12), respectively, plotted in FIG. 1A. Measurement of light absorbed at two different wavelengths can be used to obtain the blood oxygenation. The pulsatile PPG signals 14 generated by optical detection of blood volume variations due to periodic heart contractions/relaxations are used to obtain the heart rate, as shown in FIG. 1B. Since a few other physiological factors are also related to blood flow, a PPG waveform can also be used to monitor respiratory, hypovolemia, and other circulation conditions. As schematically illustrated in FIGS. 1C and 1D, state-of-the-art pulse oximeters, designated generally by numerals 16 and 18, employ a light emitting diode (LED) 4 and a photodetector (PD) 6 to measure the light transmitted through a part of the person's body, either in transmission mode (as in FIG. 1C) or reflection mode (as in FIG. 1D), depending on the measurement sites and application.

Several major limitations hinder the wide application of wearable PPG sensing:

Low Signal-to-Noise Ratio (SNR):

"Single-pixel" LED/PD sensing architectures fundamentally limit the achievable SNR of an optical sensing system, as do architectures with a small number of LED/PD pairs. A cross-sectional view of an optical sensing path 201 is shown in an example in FIG. 2A, where an optical sensing system is designated generally by numeral 200, and otherwise referred to herein as a "sensor." A complex skin microcirculation network 203 and other tissues of skin 205 in the optical path 201 introduce a significant amount of non-pulsatile background noise to the measured PPG signal. Divergence of LED light beam 210 causes further optical power loss. As a result, the measurable amplitude of the pulsatile AC signal at a person's wrist is typically only ~1% of the DC component. In operation, light 210 from a single divergent LED light source 220 is launched to probe a region 212 (shown in the top view of FIG. 2B) of the skin within which only a small portion of the region is pulsating, resulting in excessive background noises in the signal detected by photodetector 222, and inefficient usage of the light source 220. Any further variance of background conditions (e.g., ambient light illumination, motion artifacts, venous pulsation artifact due to high-skin pressure-induced venous congestion) further degrades the already low SNR and makes the readout unreliable. Some approaches adopt two, or a few, LEDs to increase the input light intensity and collects the reflected light by one photodetector (PD) 222. However, due to the fundamentally same sensing principle as that of the "single-pixel" detection architecture, such techniques provide limited improvement on SNR at the expense of significantly increased optical power consumption.

Susceptibility to Motion Artifacts:

Relative movement between the sensor and the probed region introduces optical path variance between the LED and PD, which do not align with the pulsatile objects and background tissues that are being measured originally. Such deviations usually lead to erroneous readouts and frequently happen in mobile usages, which is a leading issue for state-of-the-art wearable PPG sensors and heart monitors. Although attempts had been made to mitigate these issues using advanced signal processing and motion sensors 224 (e.g., accelerometers), the improvement is not sufficient for mobile implementations, fundamentally limited by the physical "single pixel" LED-PD sensing architecture.

Ambient Light Illumination:

For non-contact PPG sensors (including wrist band heart rate monitors that are currently commercially available), an air-gap between the sensor 200 and the skin 205 usually directly expose the PD 222 under the illumination of the LED 220 or an ambient light source (e.g., sunlight). Such undesired light exposure may overwhelm the PPG signal or saturate the PD 222, resulting in corrupted signal readouts.

Venous Pulsation Artifacts:

For measurements that require contact between the sensor 200 and skin 205, high skin pressure may cause venous congestion that leads to venous pulsation artifacts. Since the venous blood typically possesses lower HbO2 concentration than the arterial blood, such artifacts introduce inaccuracies into the measurement results.

Probing Site Restriction:

Measurement sites for transmission-type pulse oximeters are typically at fingertips, ear lobes, nasal septum, cheeks, tongues, or feet for an infant. Transmission-type pulse oximeters are capable of obtaining signals with relatively good qualities and thus are usually used in the hospital with fingertips and earlobes as preferred monitoring positions. However, the probing sites are limited to such regions with limited blood perfusion, which are more susceptible to environmental extremes, such as low ambient temperatures (possible operation conditions for military personnel or athletes in training). Another obvious disadvantage of the fingertip sensor is its interference with daily activities if utilized for continuous measurements.

Reflection-type sensors are typically applied on forehead, wrist, chest, or feet. They provide more flexibility to the implementation space and are more practical for wearable PPG sensing than transmission-type sensors. However, due to the more complex optical path, their sensing accuracy is more susceptible to external factors, such as motion artifacts and ambient illumination.

In addition, due to the complexity of other vessels and tissues under the skin, each type of pulse oximeter is only suitable for a specified application site. Inappropriate device deployment usually leads to erroneous readings.

Power consumption: As mentioned above, state-of-the-art PPG sensing techniques typically use, at most, a small number of LED/PD optical paths to probe a skin region within which only a small portion of the probed area is of interest. As a result, a vast amount of optical power is wasted to generate signals that only contribute to background noise which further degrades SNR. In addition, the necessity to include a 3D accelerometer in commercial heart-rate monitors further contribute to the overall power budget of such wearable devices with limited performance improvement.

Finally, state-of-the-art pulse oximeters and heart-rate monitors are typically enclosed within a rigid, non-conformal module, due to the tight alignment tolerance between sensor and the skin.

One review of the state of the art is provided by Tamura, et al. "*Wearable photoplethysmographic sensors—past and present,*" *Electronics*, vol. 3, pp. 282-302, (2014), which is incorporated herein by reference. A PPG array sensor module is described by Lee, et al., "*Development and Evaluation of a Wristwatch-Type Photoplethysmography Array Sensor Module,*" *IEEE Sensors Journal*, vol. 13, pp. 1459-63 (2013), which is also incorporated by reference. The array sensor module of Lee is necessarily limited to a small number of sensors.

It would be desirable to provide a versatile photoplethysmographic technology suited to application at measurement sites characterized by distinct contour shapes, while, at the same time, exceeding the performance of current photoplethysmographs (PPGs) with respect to optical efficiency and signal-to-noise. Such a PPG is provided for the first time in accordance with the present invention, as described below.

SUMMARY OF EMBODIMENTS OF THE INVENTION

In accordance with embodiments of the invention, a novel ultra-compact bio-optical sensing platform is described. Embodied as a wearable PPG pulse oximeter, it is designed to measure blood oxygen saturation ($SpO_2$), heart rate (HR), and respiration in intense motions with high reliability through differential optical probing of a variety of vascular elements, such as blood vessels positioned at different depth under the skin, e.g., arteries (>2 mm in depth) and capillaries (~200 μm in depth). The optical sensing platform may also serve as a planar integrated speckle imaging system for measuring blood flow properties. The optical sensing system consists of a light source (micro-LEDs, lasers, for example) and PD arrays linked by micro-optic-coupled optical probing and detection channel arrays. A novel method is also described that is based on the multi-channel bio-optical sensing approach for biological tissue detection, identification, sensing, and tracking.

According to one aspect of the present invention, there is provided a sensor for non-invasively monitoring a characteristic of an organism. The sensor, which may be a photoplethysmograph, has a plurality of light sources disposed upon a substrate and an array of optical probing channels for conveying light from the plurality of light sources to a probed region. Additionally, the sensor has an array of detector pixels, each detector pixel of the array of detector pixels receiving light from a respective optical detection channel after interaction with the probed region and spatial filtering and generating a corresponding pixel signal. Finally, the sensor has a processor for deriving a value of the characteristic of the organism based at least upon the plurality of pixel signals.

In accordance with other embodiments of the invention, the substrate may be conformally deformable or rigid. At least one of the array of optical probing channels may include a waveguide. An array of waveguides may be provided for guiding light, at least in part, from the plurality of light sources to the probed region.

In further embodiments of the invention, light may be guided from the plurality of light sources to the probed region, at least in part, by an array of free-space optical components, or by more than one of the optical probing channels of the array of optical probing channels. Light may also be guided from the probed region to the array of detector pixels at least in part by an array of waveguides or, at least in part, by an array of free-space optical components.

In other embodiments of the invention, the sensor may also have a modulator for modulating a property of the light from at least one of the plurality of light sources. The modulated property may be beam intensity, beam phase, or polarization. The plurality of light sources may include LEDs or coherent light sources. Additionally, each detector pixel of the array of detector pixels may correspond to a distinct subregion of the probed region in 3-dimensional space, such as a specific depth within the probed region, or to a distinct point of an interference pattern formed by scattered light from multiple subregions of the probed region.

In yet other embodiments of the invention, each optical probing channel has an optical coupling structure for illuminating a subregion of the probed region. Each optical detection channel may have an optical coupling structure designed to receive a subregion of the probed region.

In accordance with another aspect of the present invention, a method is provided for non-invasively sensing features of a sample. The method has steps of:

a. generating light by means of a plurality of light sources disposed upon a substrate;

b. illuminating a probed region of the sample with the light from a plurality of light sources or light source channels via an array of optical probing channels;

c. generating a plurality of detector signals based on spatially filtered light conveyed from the probed region to an array of detector pixels; and d. sensing a specified feature of the sample by processing the plurality of detector signals.

In further embodiments, sensing the specified feature may include temporally resolving evolution of the plurality of detector signals. The specified feature may include a vital body sign. Illuminating the probed region of the sample may include coupling light out of the array of optical probing channels to generate an array of beams incident upon the sample as well as temporally modulating a property of the light from the plurality of light sources.

In accordance with other embodiments of the present invention, each detector pixel of the array of detector pixels may correspond to a subregion of the probed region of the sample, and, more particularly, the correspondence to a subregion of the probed region may be unique. Each detector pixel may correspond to a point of a pattern formed by scattered light from multiple subregions of the probed region of the sample.

In yet further embodiments, illuminating the probed region of the sample may include coupling light out of the array of optical probing channels in such a manner that light emerges from distinct optical probing channels with a plurality of focal properties. Sensing the specified feature may include discriminating between the specified feature and any background feature based on a specified spatial or temporal characteristic of the specified feature. Sensing the specified feature may also include dynamically assigning distinct optical probing channels to distinct monitored features of the sample, or binning data from a specified subset of detector pixels to enhance measurement accuracy. Sensing the specified feature may also include analyzing the temporal and spatial variance of the speckle pattern formed by interference from scattered light.

In still other embodiments, generating light by means of the plurality of light sources may include selectively governing optical power output of distinct light sources of the plurality of light sources in order to selectively enhance signal from specified subregions of the probed region of the sample.

In accordance with another aspect of the present invention, a computer-implemented method is provided for deriving a specified characteristic of a biological organism. The method has steps of:

a. coupling light from a plurality of light sources to illuminate a portion of the biological organism with a two-dimensional light beam array;

b. coupling spatially filtered light from the two-dimensional light beam array, after interaction with subregions of the biological organism, to a photodetector pixel array;

c. generating a cube of data based on detection of light having interacted with subregions of the biological organism; and d. selecting data from the cube of data relative to specified features of the biological organism to derive a specified characteristic of the biological organism.

In further embodiments of the invention, the cube of data may be indexed on the basis of a depth- and spectrally-resolved two-dimensional array. A first subset of the cube of data may be associated with target tissue and a second subset of the cube of data may be associated with background tissue. The method may have a further step of dynamically varying optical power within elements of the two-dimensional light beam array on the basis of identified features illuminated by respective elements of the two-dimensional light beam array.

In yet another aspect of the present invention, a method is provided for non-invasively sensing features of a sample, the method comprising:

a. generating light by means of a plurality of light sources or light source channels disposed upon a substrate;

b. illuminating a probed region of the sample with the light from a plurality of light sources via an array of optical probing channels;

c. generating a plurality of detector signals based on spatially filtered light conveyed from the probed region to an array of detector pixels over a period of time; and d. sensing the movement of the sample by processing the temporal and spatial variance of the plurality of detector signals.

In further embodiments, the light sources may emit coherent light, and an interference pattern may be formed by scattered or reflected light from the sample is captured by the optical detection channels and conveyed to the detector pixel array. Information related to sample movement may be obtained by analyzing temporal and spatial variations of the captured interference pattern.

According to another aspect of the invention, a method is provided for reducing background noise using the optical sensing system. Since the computer program can differentiate regions containing target blood vessels from other tissues based on the output from the optical sensing system, the optical channels probing subregions recognized as target biological tissues (e.g., arterial vessels) may be selected for sensing data retrieval, thus reducing the non-pulsatile background noise contributed by unrelated tissues and/or venous pulsation artifacts. The SNR can be further improved by measuring the background noise, ambient illumination, and/or venous pulsation components captured from surrounding regions and subtract them from the pulsatile AC signal.

According to another aspect of the invention, a method is provided for intelligent power management using the optical sensing system. Since the computer program can differentiate regions containing target blood vessels from other tissues based on the output from the optical sensing system, the optical sensing system may dynamically and selectively turn off light sources or optical channels that illuminate regions not of interest to the current measurement. The optical sensing system may also selectively increase optical power of one or several light sources or optical channels for regions of particular interest and/or reduce the power of sources or channels of less interest to improve the overall SNR and measurement accuracy. Such versatile strategies cannot be implemented by conventional PPG approaches due to the single- or few-pixel sensing architecture and the limited power budget.

According to another aspect of the invention, a method is provided for high-precision sensing based on data-fusion using the optical sensing system. The multi-channel sensing architecture of the invention allows integration of data from multiple channels with low SNR to reconstruct high-SNR, high-fidelity measurement results. Data collected from optical channels probing a similar type of tissue or tissue combinations may be combined or analyzed collectively to enhance measurement accuracy of a certain type of tissue or tissue combination. For example, PPG data collected from blood capillaries are typically considered less accurate than data collected through arteries and are easily compromised by the existence of other tissues. By pixelating the sensing region and selecting subregions that are mostly dominated by capillary absorption, data retrieved from such channels are decoupled from other tissues and can be fused together and reconstructed to provide a more reliable readout of the capillary-related absorption with enhanced SNR.

According to another aspect of the invention, a method is provided for performing speckle imaging using the optical sensing system. One or a plurality of probing optical channels coupling light from light sources (e.g., waveguide or free-space optical coupling channels) are configured as one or an array of coherent light sources to illuminate a portion of the biological organism; the reflected light is collected by the optical detection channels and detected by the photodetector array. As the coherent light is scattered by a random medium populated with scatterers, a random interference patterns (i.e., speckle pattern) is generated. When the scatterers (such as red blood cells in blood vessels) move, the scattered light experience phase shifts which induce fluctuations of the speckle pattern. Blood flow can be characterized by analyzing the temporal and spatial variation of the speckle pattern generated using the optical sensing system. This approach also allows the identification of blood vessels from other biological tissues that have different scattering properties.

BRIEF DESCRIPTION OF THE DRAWINGS

The foregoing features of the invention will be more readily understood by reference to the following detailed description, taken with reference to the accompanying drawings, in which:

FIG. 3A shows a schematic cross section of a multichannel optical sensing system in accordance with an embodiment of the present invention, while

DETAILED DESCRIPTION OF EMBODIMENTS OF THE INVENTION

Definitions

Figure 1A:
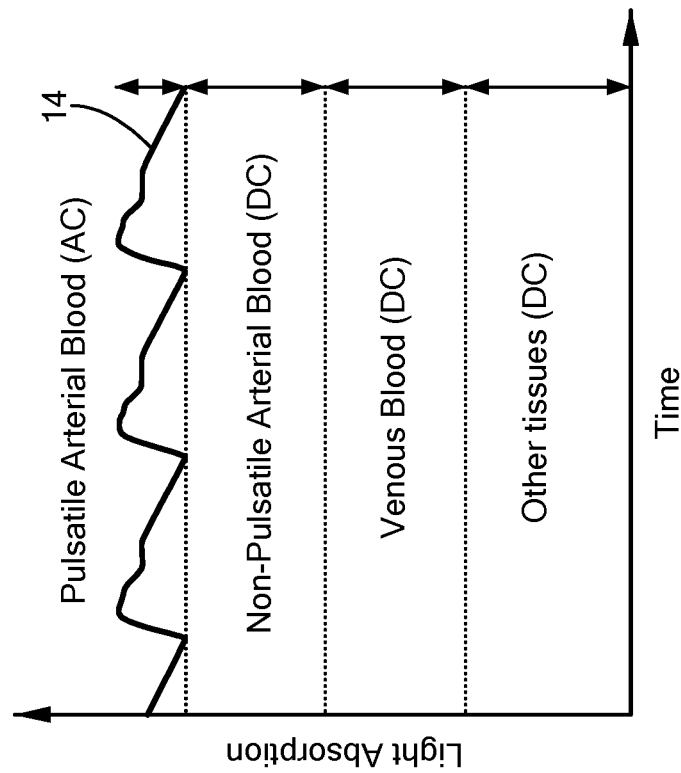
FIG. 1A depicts respective absorption spectra of oxygenated and deoxygenated hemoglobin.
Figure 1B:
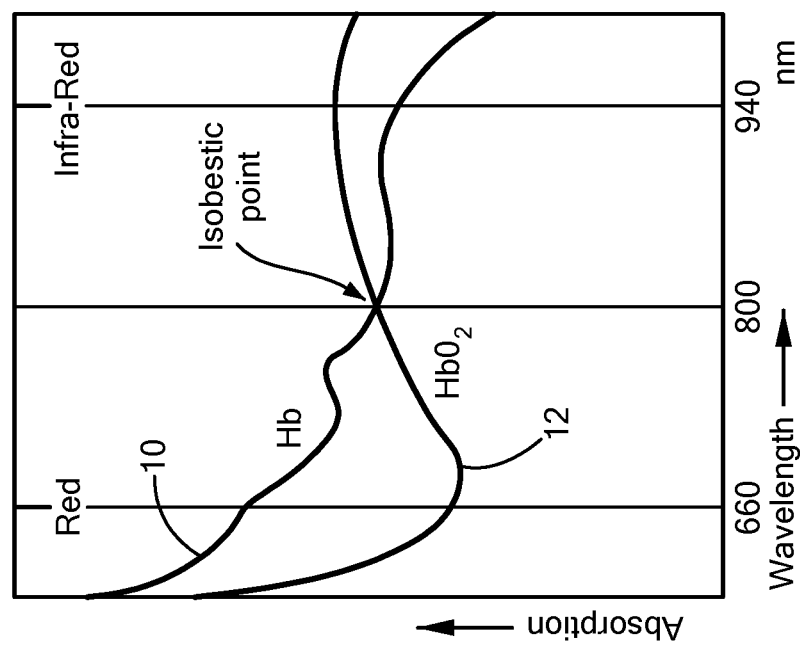
FIG. 1B depicts a PPG waveform generated by optical detection of blood volume variations due to periodic heart contractions and relaxations.
Figure 1C:
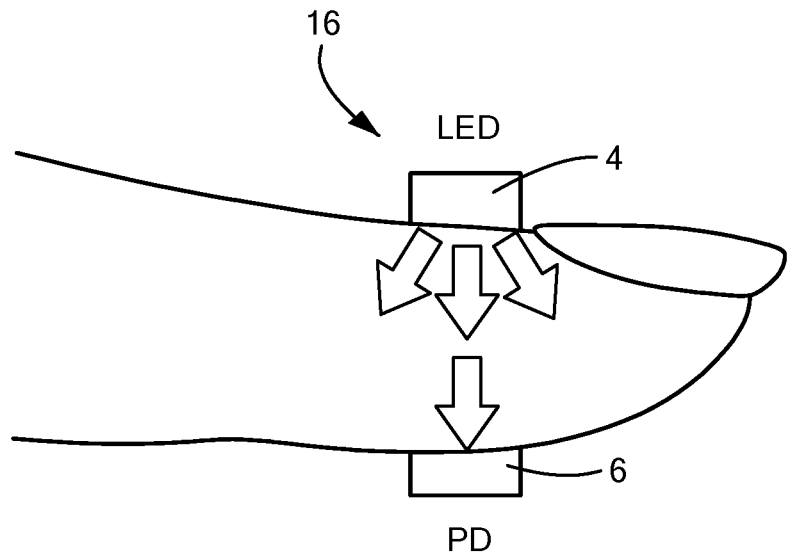
FIGS. 1C and 1D depicts respective transmission and reflection variants of prior art PPG embodiments.
Figure 1D:
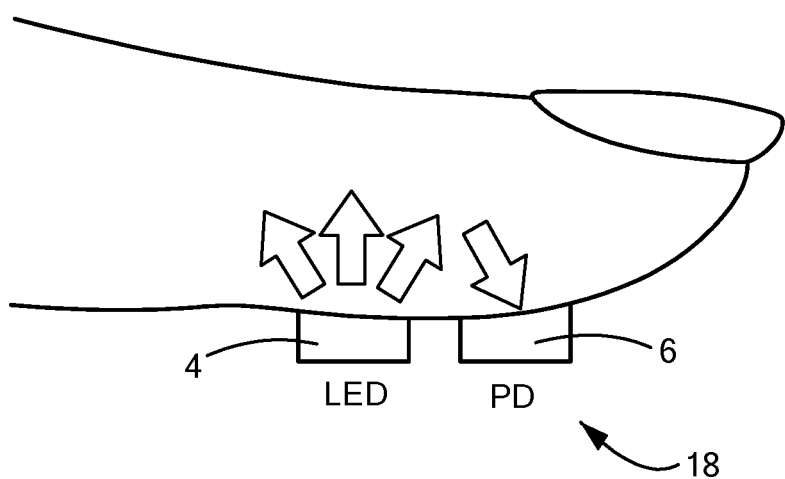
Figure 2B:
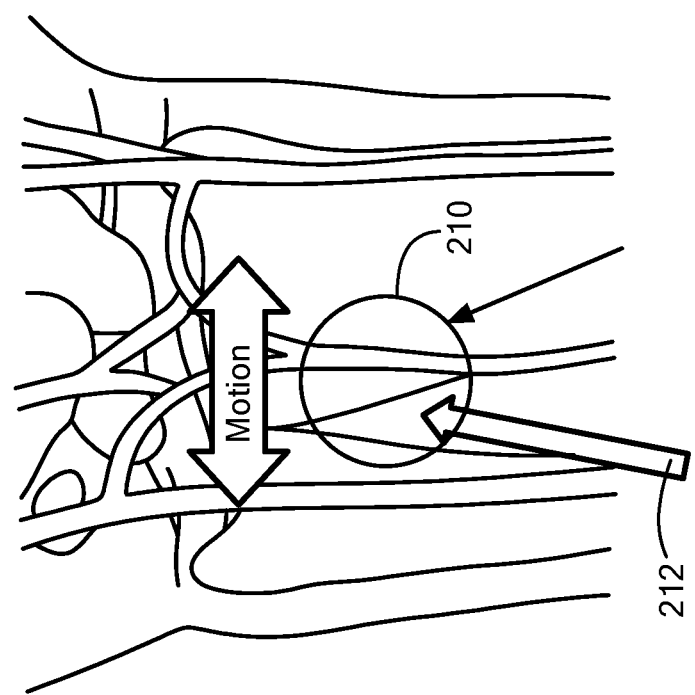
FIG. 2B depicts a zone monitored by the prior art monitor of FIG. 2A, as seen from the top of a sampled region.
Figure 2A:
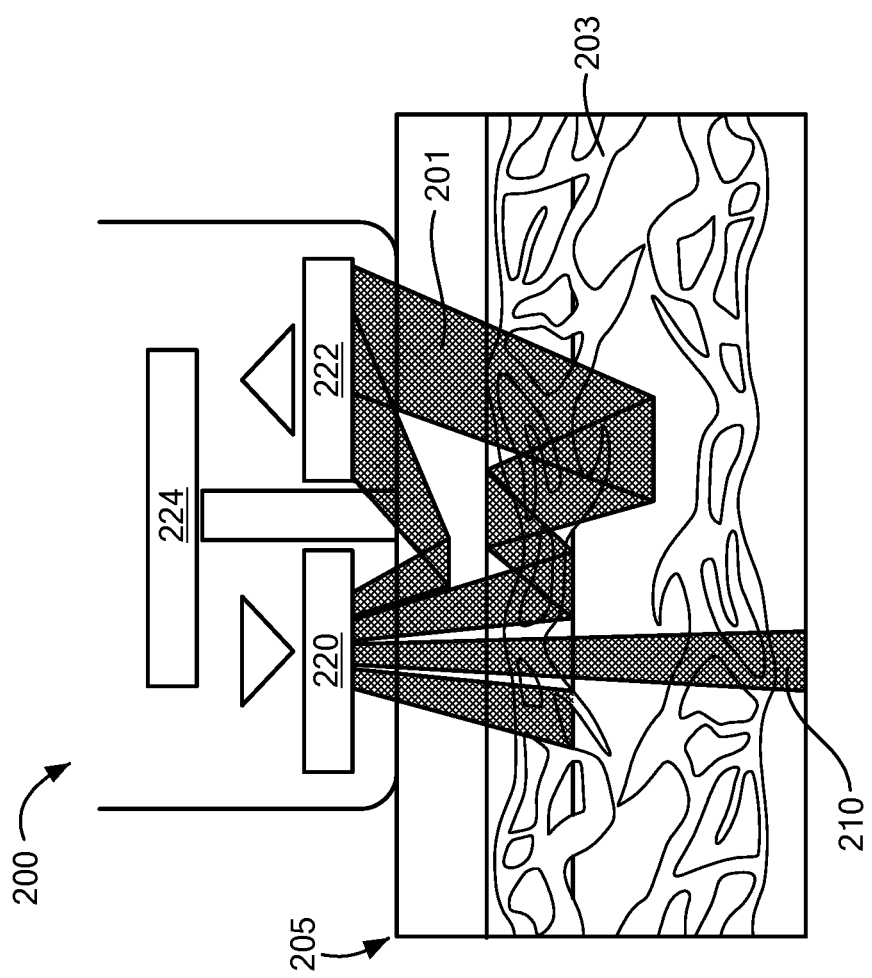
FIG. 2A depicts a cross-sectional schematic view of a prior art wearable heart-rate monitor.

As used herein and in any appended claims, the term "photoplethysmography sensor" (PPG sensor) shall be construed broadly to encompass any instrument that employs light to ascertain one or more characteristics of blood flowing within live tissue. The terms "light," and "optical," as used herein, are not limited with respect to spectral content, and may encompass electromagnetic radiation in the visible, ultraviolet or infrared portions of the electromagnetic spectrum, as suited to a particular application. Characteristics associated with blood flowing within live tissue include, by way of example, but without limitation:

Blood oxygen saturation
Blood pressure
Blood glucose
Cardiac output
Heart rate
Respiration
Vascular assessment
Arterial disease
Arterial compliance and ageing
Venous assessment
Endothelial function
Microvascular blood flow
Vasospastic conditions
Autonomic function monitoring
Vasomotor function and thermoregulation
Blood pressure and heart rate variability
Orthostasis
Cardiovascular variability assessments.

The foregoing characteristics are examples of characteristics of an organism, values of which may be determined in accordance with embodiments of the present invention. Some such characteristics are categorized as vital signs, however practice of the present invention is not limited to the measurement or characterization of vital signs.

An "optical channel," as the term is used herein, refers to a specified path for propagation of a beam of light, and may include a path through free space or through a medium in which the light propagates in an unguided manner, including free-space optical structures, such as lenses, mirrors, diffractive optical elements, sub-wavelength optical elements, etc., or, alternatively, a propagation path in which a light beam is guided, in whole or in part, by optical waveguide or fiber. Optical channels include both optical probing channels between the sources and a probed region and optical detection channels between the probed region and detector pixels.

"Spatial filtering," as the term is used herein, shall refer to constraining the energy distribution of light detected from a region to a specified range defined within a transform space. Thus, for example, either waveguides or lenses serve to limit the distribution of light in a spatial transform space and thus to spatially filter detected light.

A "sample," as the term is used herein, shall refer, without limitation, to any probed specimen, including, but not limited to, biological tissue.

An "array," as the term is used herein, shall refer to a physical (and not abstract) structure possessing a characteristic spatial periodicity in at least one dimension.

"Conformal deformable" shall denote that a structure may be deformed in such a manner as to preserve the shape of any infinitesimally small figure on the surface of the structure.

The term "image" shall refer to any multidimensional representation, whether in tangible or otherwise perceptible form, or otherwise, whereby a quantity (which may, itself, be a scalar, spinor, vector, tensor, etc.), associated with some characteristic (amplitude, phase, polarization, etc.) is, in turn, associated with each of a plurality of locations corresponding to dimensional coordinates of an object in physical space, though not necessarily mapped one-to-one thereon. Thus, for example, the graphic display of the spatial distribution of some field, scalar or vectorial, such as brightness or color, constitutes an image. So, also, does an array of numbers, such as a 3D holographic dataset, in a computer memory or holographic medium. Similarly, "imaging" refers to the rendering of a stated physical characteristic in terms of one or more images.

A 'cube' of data, as the term is used herein, is an n-dimensional array of quantities associated with a probed object, where the quantities (which may be scalar, spinor, vector, tensor, etc.), assume values associated with each of a plurality of loci within the n-dimensional array.

Multi-Channel Bio-Optical Sensing System

Figure 3A:
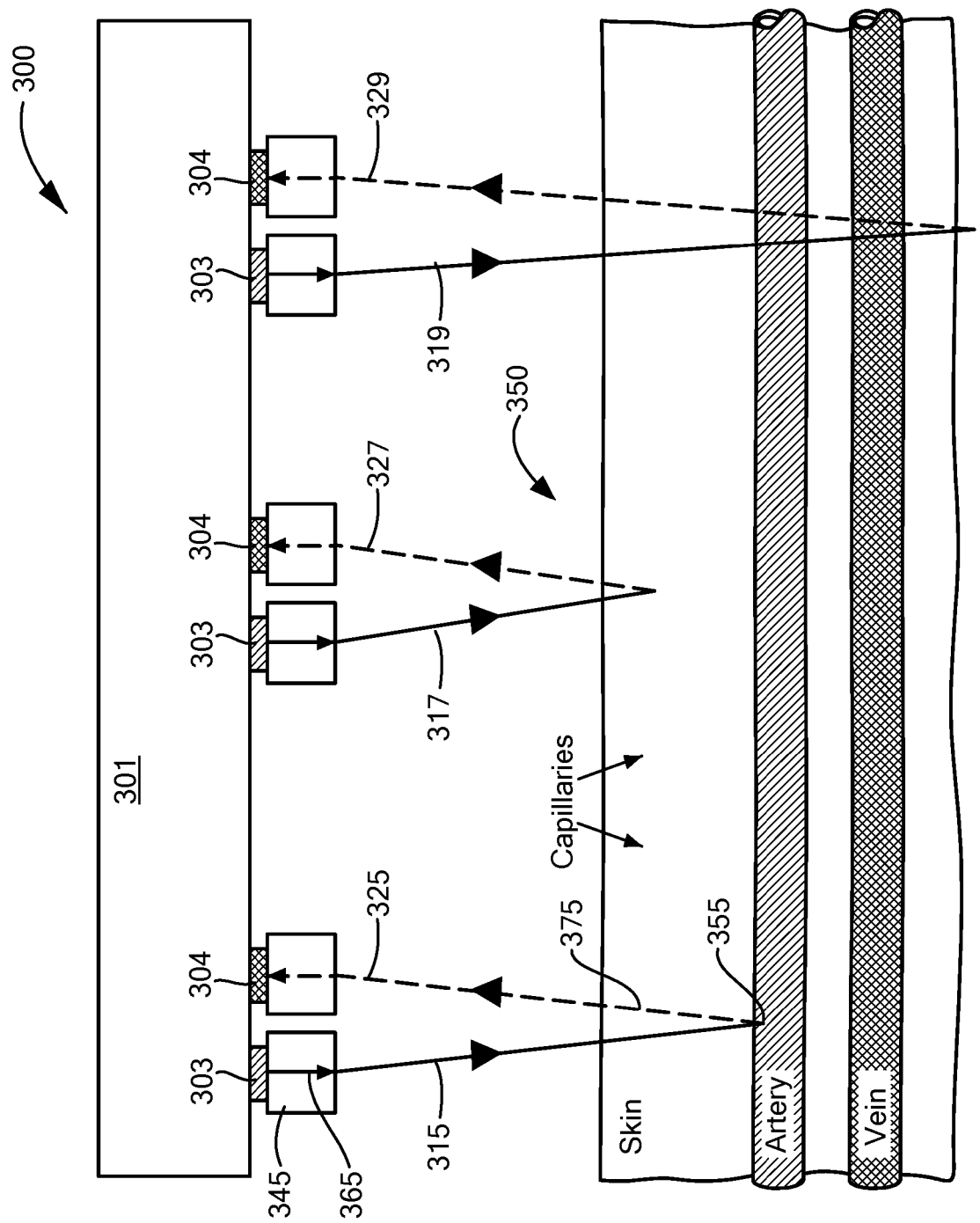
Figure 3B:
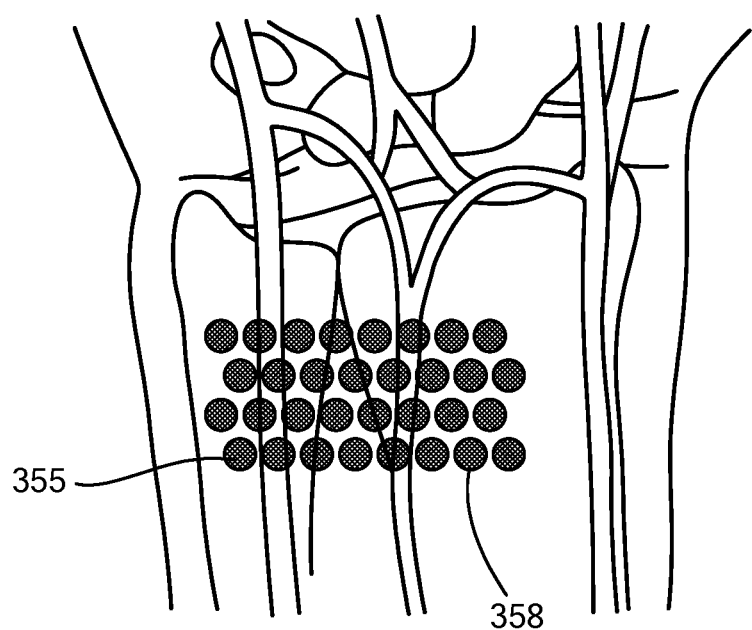
FIG. 3B depicts probed subregions monitored in accordance with an embodiment of the present invention, as seen from the top.

In accordance with embodiments of the present invention, a multi-channel bio-optical sensing system, otherwise referred to herein as an "optical sensing system," and designated generally by numeral 300, is initially described with reference to FIGS. 3A and 3B. As illustrated schematically in FIG. 3A, salient components of the optical sensing system 300 include a substrate 301 (or, alternatively a superstrate, however the term "substrate" will be used to encompass both, as a matter of convenience), one or a plurality of light sources 303, a photodetector pixel array 304, and a plurality of optical channels. The plurality of light sources 303 are preferably configured as an array, and may be referred to herein collectively as source array 303. The optical channels may include an array of optical probing channels 315, 317, 319 and/or an array of optical detection channels 325, 327, 329. The set of optical probing channels 315, 317, 319 may be referred to herein collectively as optical probing channel array 315, and, mutatis mutandis, optical detection channels 325, 327, 329 may be referred to herein collectively as optical detection channel array 325.

In some embodiments, one optical channel may serve as the functionalities of both optical probing and detection. One or more light sources 303 emit beams 365 that are coupled through the optical probing channel arrays 315 and directed to a region of interest 350 for sensing (such as a region of human skin) by optical coupling elements 345.

The path of each beam 365 from light source 303 (which may otherwise be referred to herein simply as a 'source') to region of interest 350 is referred to as the optical probing channel 315. The region of interest 350 may be referred to herein, as well, as the "sensed region." The optical probing channels 315, 317, 319 represent a two-dimensional (2-D) array of paths of optical probing beams onto the region, each of which is incident on a subregion 355 for sensing.

The probing beams of the probing beam array propagate through the sensed region 350 (e.g., blood vessels, skins, muscles, etc.) and interact optically with biological tissues encompassed within the sensed region 350 via modalities of light-matter interaction such as absorption, refraction, or reflection. After optical interaction with the sensed region 350, each beam 375 of the array of beams emanating from the sensed region 350 is subsequently collected by an optical detection channel 325 in the detection channels array that receive either reflected or transmitted light from the sensed subregion.

Optical coupling element 345 includes any optic, transmissive or reflective, that varies the transverse phase characteristics of a beam that traverses it. Optical coupling elements 345 in the optical channels may be configured to optically probe and detect biological tissues with different types, size, and depth under the skin. For example, a curved reflective mirror is formed at one end of an optical probing waveguide to focus the probing beam to a sample point; the reflected beam is received by an optical detection waveguide via a similar reflective mirror that redirects the light into the detection waveguide. The optical detection channels 325, 327, 329 then couple the light to a photodetector pixel array, with each beam (and the corresponding subregion probed) registered to a photodetector pixel. Optical probing channels 315 and optical detection channels 325 may be referred to herein collectively as optical channels 315, 325. Optical sensing system 300 thus divides and pixilates the total region of interest 350 into a 2D array (designated generally by numeral 358) of multiple subregions 355, shown as well in the top cross-sectional view of FIG. 3B, and probes and senses each subregion individually. In another embodiment of the present invention where the optical sensing system is used for speckle imaging, one or multiple optical probing channels 315 are configured as coherent sources and illuminate a region of interest 350. The light scattered by multiple subregions 355 form an interference pattern on the photodetector pixel array 304 via the optical detection channels 325. Light sources 303 that emit multiple wavelengths, whether spectrally contiguous or not, may be coupled into the optical channels 315 within the scope of the present invention.

Substrate 301 may be rigid, flexible, stretchable, or conformal to the surface to which it is applied, within the scope of the present invention. Light sources 303, photodetector array 304, and optical channels 315, 325 may be disposed on the substrate/superstrate 301. Light sources 303 may be light emitting diodes (LED), or lasers, for example. Light source array 303 may include individual light sources emitting at wavelengths that differ among the different light sources. Light source 303 may also consist of broadband or wavelength-tunable light sources, within the scope of the present invention. Optical channels 315, 325 may be in the form of waveguide structures, free-space optical structures, or a combination of the two approaches. In either case, when the energy distribution of light detected from a region or subregion is constrained, in transform space, the light from that region or subregion may be said to be spatially filtered.

Figure 4:
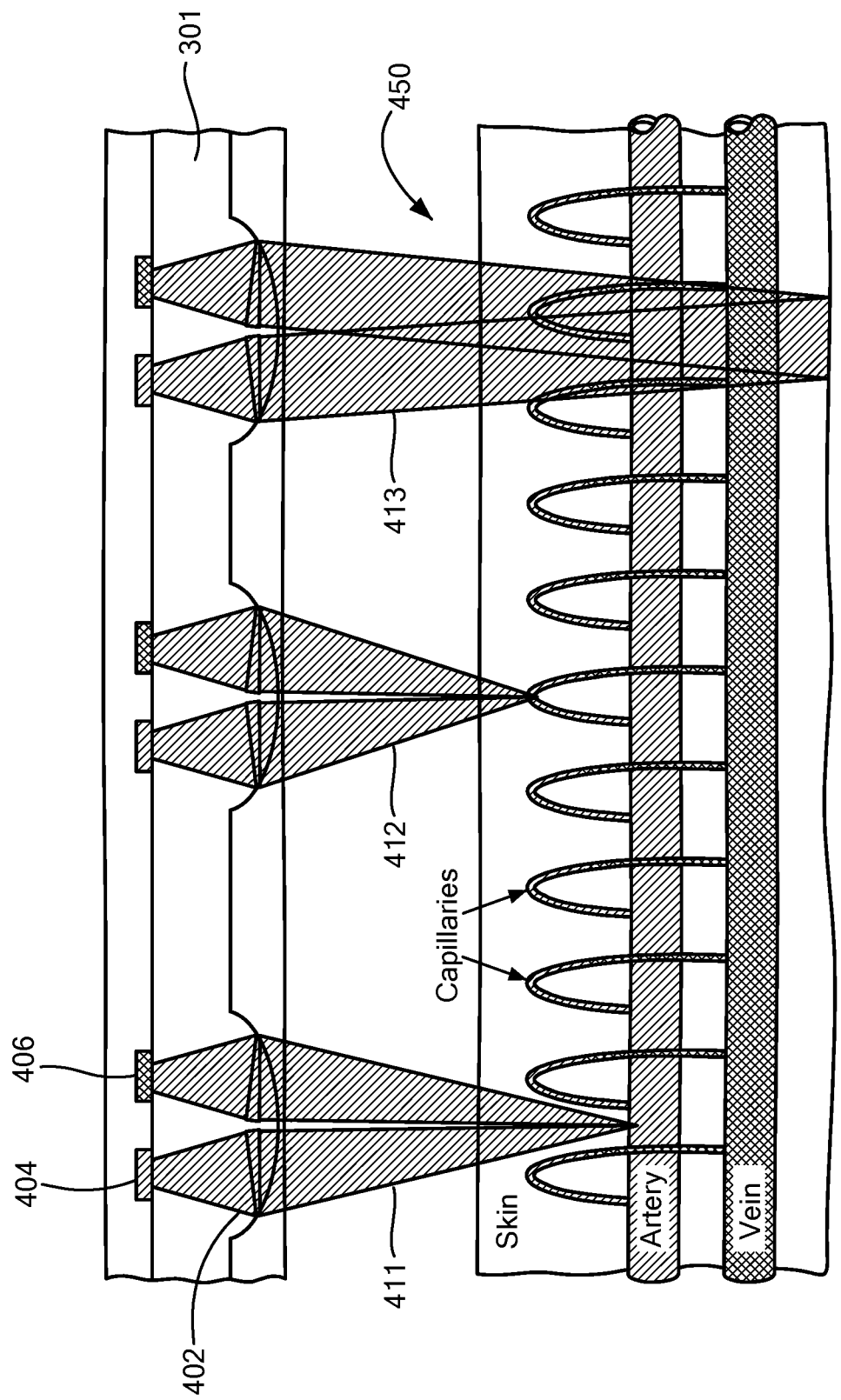
FIG. 4 schematically depicts multiple probing light beams emitted by an array of micro-LEDs and coupled by microlenses configured to have different focal lengths and illumination patterns, in accordance with an embodiment of the present invention.

For free-space channels, optical coupling elements 345 such as lenses 402, mirrors, diffractive optical elements, or sub-wavelength optical elements may be used to couple the light emitted from a light source 404 to illuminate an area of biological tissue of interest 450, as schematically depicted in one embodiment shown in FIG. 4. The same or another optical coupling element 345 may be used as the optical detection channel to couple the light reflected or transmitted from the probed region, spatially filtered, to a photodetector 406. Lenses 402 may include microlenses, and may be configured to provide a variety of focal length and illumination patterns (e.g., focused, collimated, structured illumination patterns, or any desired illumination pattern) to probe tissues with different types and sizes and at different depths. As a result of spatial filtering, the probed sub-region illuminated by the probing channel may advantageously be accurately correlated with the detection channel and thus detector pixel, with minimal noise and unrelated information coupled into the detection channel.

For waveguide-based optical probing and detection channels, light sources 404 (e.g., a micro-LED array) are first coupled into a probing waveguide array. A single light source may be split and distributed into multiple channels 411, 412, and 413. The light beam in each channel is subsequently coupled out of the channel by one or a plurality of waveguide coupling structures (such as waveguide facet couplers, diffractive optical elements, gratings, sub-wavelength optical elements, etc.) to generate an array of beams that illuminate an area of tissue of interest. Each probing channel illuminates a subregion or multiple subregions of the total sensed region. The waveguide coupling structures may be configured to provide a variety of focal length and illumination patterns (e.g., focused, collimated, structured illumination patterns, or any desired illumination pattern) to probe tissues with different types and sizes and at different depth. After transmitting inside the tissue, the reflected beam array with modulated beam properties (e.g., intensity variance due to tissue absorption, phase shifts, or polarization change) by the corresponding subregions are coupled back into a corresponding detection waveguide array and directed to the photodetector pixel array, with each beam (and thus subregion probed) registered to a photodetector pixel 406. In another example, coherent light scattered by multiple subregions form an interference pattern that is collected by the detection waveguide array and directed to the photodetector pixel array.

Figure 5A:
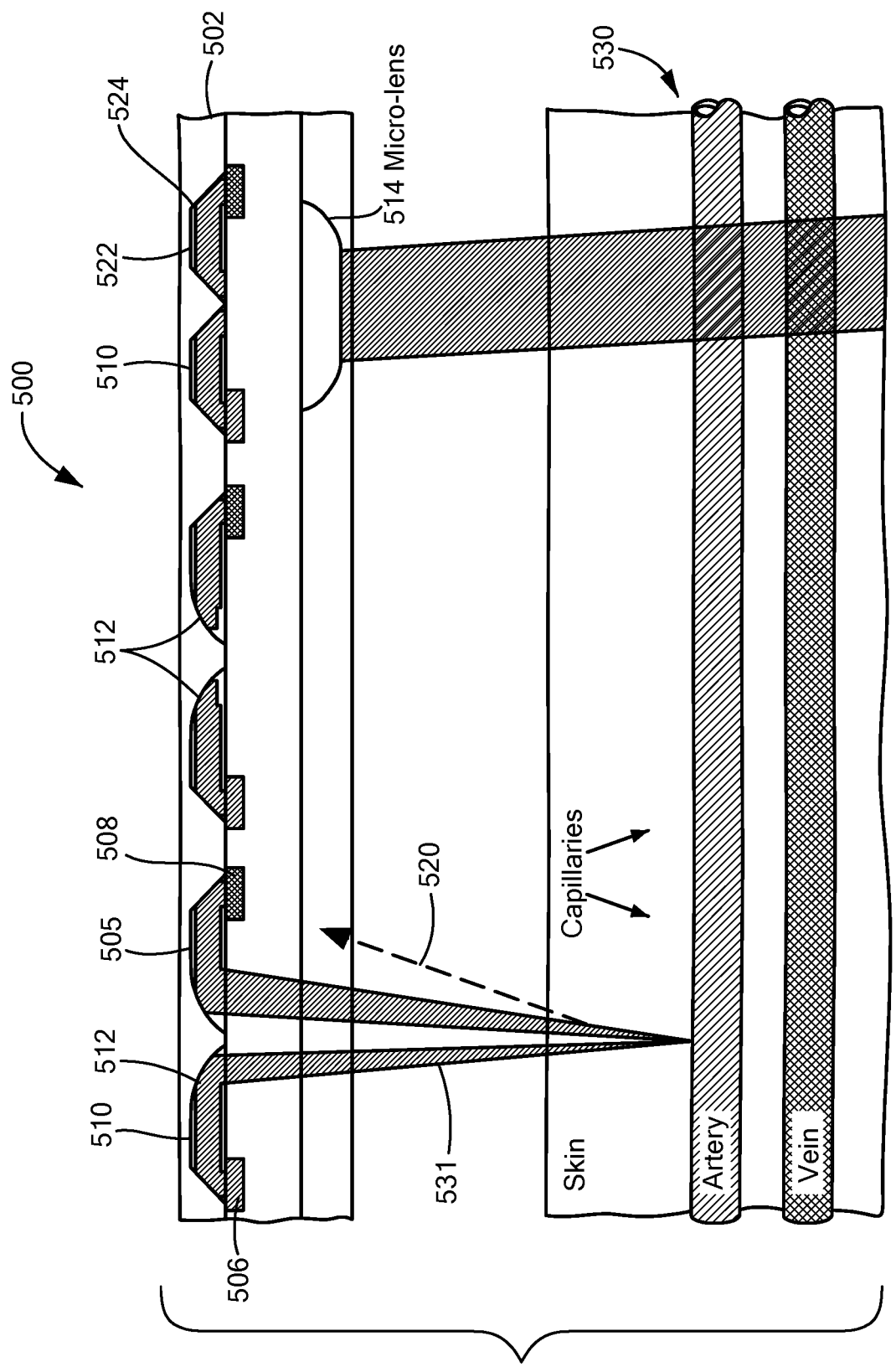
FIG. 5A depicts a schematic cross-section of a multichannel optical sensing system in accordance with an embodiment of the present invention.
Figure 5B:
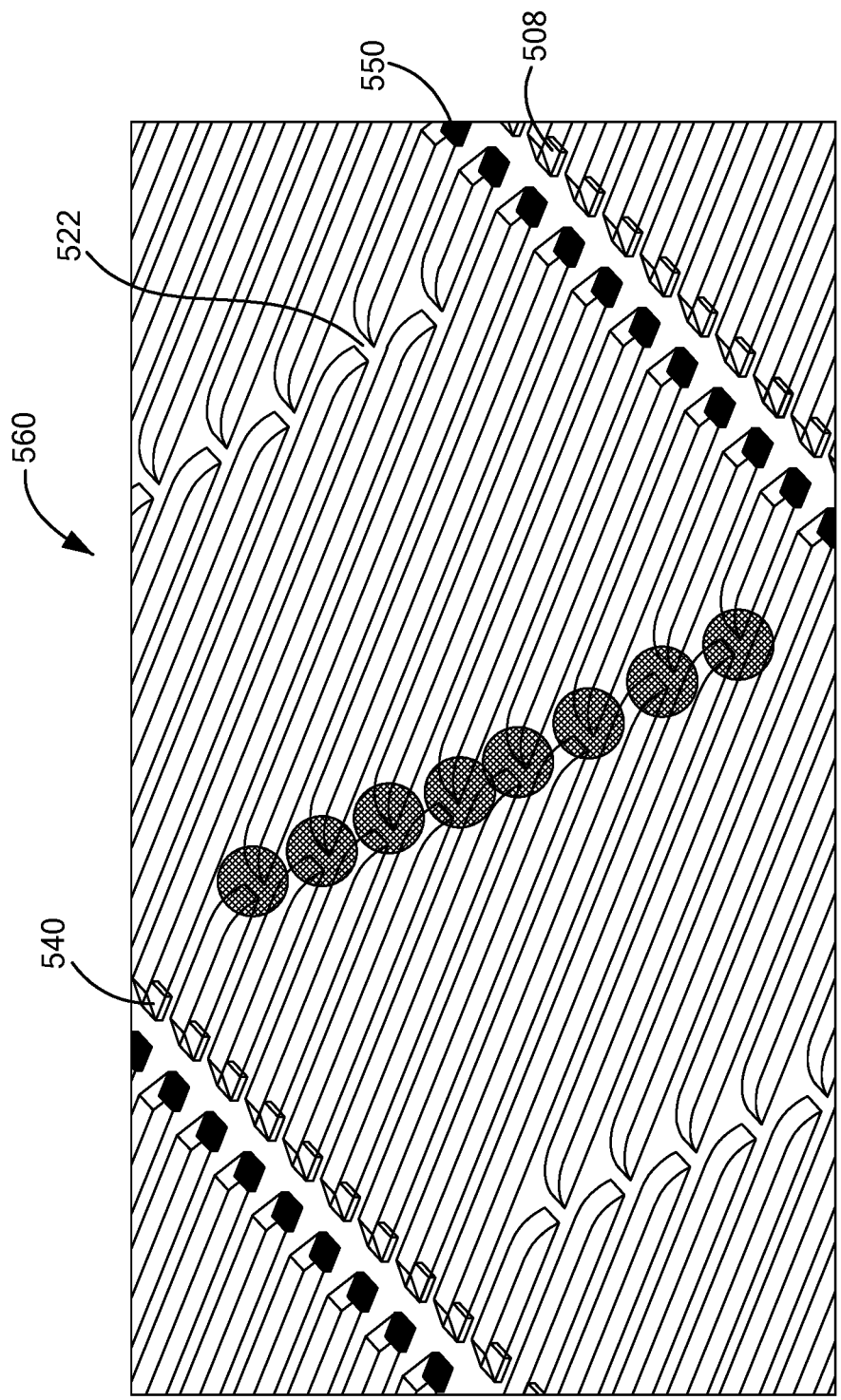
FIG. 5B is a perspective view of the embodiment of FIG. 5A.

One embodiment of a bio-optical sensing system, designated generally by numeral 500, is now described with reference to FIGS. 5A and 5B. Salient features of bio-optical sensing system 500 may include:

- a substrate 502 (made of polymer such as PDMS, for example) that may be flexible and/or stretchable;
- one or more arrays 540 of light sources (e.g., micro-LEDs) 506 that may emit light at different wavelengths (e.g., a 3-wavelength sensing approach including 569 nm, 660 nm and 940 nm emission and detection) that are guided in separate waveguide channels 505 or multiplexed in each single waveguide channel;
- one or more arrays 550 of photodetector 508; and
- a 2-D waveguide array network designated generally by numeral 560, comprised of waveguides 510 that guide and couple an array of probing light beams (LED beam, for example), via separate sensing channels 531, to different subregions of the skin using micro-optical elements (e.g., curved facet couplers 512, micro-lenses 514, diffractive optical elements, gratings, holography, sub-wavelength optical elements, etc.). Reflected beams 520 from body tissues 530 are further confocally coupled into a corresponding detection waveguide 522 channel by another optical coupling structure 524 and delivered to the pixel array 550 of photodetectors 508.

Compared to conventional pulse oximeter approaches based on "single pixel" illumination, the present invention utilizes a 2D imaging sensor array architecture that pixelates the sensing region 350 (shown in FIG. 3). Advanced guided-wave micro-optic array are employed to bring confocal imaging onto the skin surface to enable spatial-temporal mapping of vascular elements and other tissues. By using different optical coupling structures (e.g., curved waveguide facets, micro-lenses, diffractive optical elements, micro-prisms, gratings, holography, sub-wavelength optical elements, etc.), the waveguide micro-optical probes are designed with a variety of focal depths (~100 μm to a few mm) and illumination patterns (beam spot sizes range from a few micron to on the order of hundreds of micron)—a key feature that allows probing different tissues at different depths, including arteries, veins, capillaries and other tissues. 3-D optical simulations and preliminary fabrication results indicate that high optical coupling efficiency can be achieved.

In accordance with embodiments of the present invention, the micro-optic-coupled sensor arrays 560 illuminate a skin region and generate a 2-D depth-resolved spatial-temporal transmission data matrix of the region with spectral information, which allows identification of tissues underneath owing to their specific characteristics under PPG. By separately probing tissue regions generating pulsatile AC and non-pulsatile DC signals, SNR is greatly enhanced compared to single-pixel approaches that look for a small pulsatile variation over a large complex background. The waveguide micro-optical coupling structures act as efficient confocal imagers, thereby spatially filtering out noises from background and ambient light and suppressing inter-channel cross-talk. LED and PD arrays are optically isolated to eliminate any direct illumination inevitable to existing technologies.

Since the region of interest is recognized and pinpointed, the approach described herein in accordance with the present invention may advantageously precisely track a target (such as an artery) using pattern recognition algorithms and eliminate motion artifacts without using a motion sensor—a key barrier for existing techniques to truly realize wearable sensing. Probing channels are dynamically assigned to different tasks, such as optical sensing, blood vessel detection/tracking, and background noise detection. A power management scheme is adapted to dynamically turn ON/OFF light source-powered optical channels to only probe the regions of interest, thereby improving power efficiency. A single light source may also be divided into many channels to simultaneously illuminate multiple sites.

Figure 6:
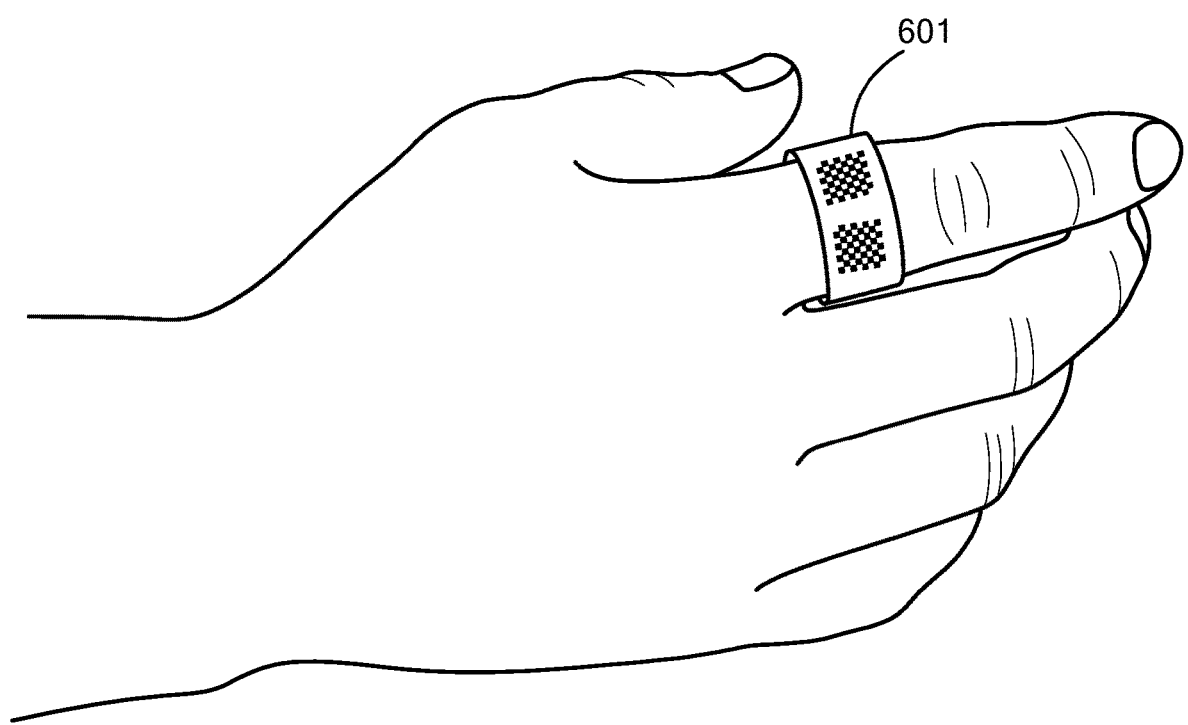
FIG. 6 depicts an optical sensing system in accordance with an embodiment of the present invention deployed as a ring-type sensor.

The ultra-thin form-factor (<100 μm thick for the light source, PD and waveguide layers) optical sensing system 500 (shown in FIG. 5A) comprising light sources (micro-LEDs, for example) and photodetector arrays, planar waveguides and micro-optic couplers, may be integrated on a flexible, stretchable, or conformal substrate 601, as shown in an example in FIG. 6. Spiral-shaped waveguides fabricated on a stretchable elastomer substrate (e.g., PDMS) can be used to provide light coupling between light sources (e.g., micro-LEDs) and photodetector arrays positioned on the same substrate. Multiple layers of waveguides and claddings can be stacked vertically to further increase the channel number. The optical performance of the micro-scale optoelectronic and optical devices is inherently much more tolerant of extreme mechanical deformations than their macro-counterparts. Embodiments of the invention which have been described in detail herein may advantageously enable applications that cannot be achieved using existing technology.

Bio-Optical Sensing by Speckle Pattern Analysis

Techniques employing speckle pattern analysis for sensing specified biological features, such as blood movement, are notoriously well-known and are reviewed in such references as Briers, "*Laser Doppler, speckle and related techniques for blood perfusion mapping and imaging*" *Physiological Measurement*, vol. 22, pp. R35-R66, (2001), which is incorporated by reference. Such techniques include analyzing the temporal and spatial variance of the speckle pattern formed by interference from scattered light. The present invention describes a novel method and apparatus for generating and detecting speckle images using the above-described optical sensing system with light sources and photodetectors positioned and integrated on a single common plane. Speckle pattern analysis techniques using the device features which have been described above may be accomplished by a reader of ordinary skill in the art and requires no further description here.

Methods of Bio-Optical Sensing

Figure 7:
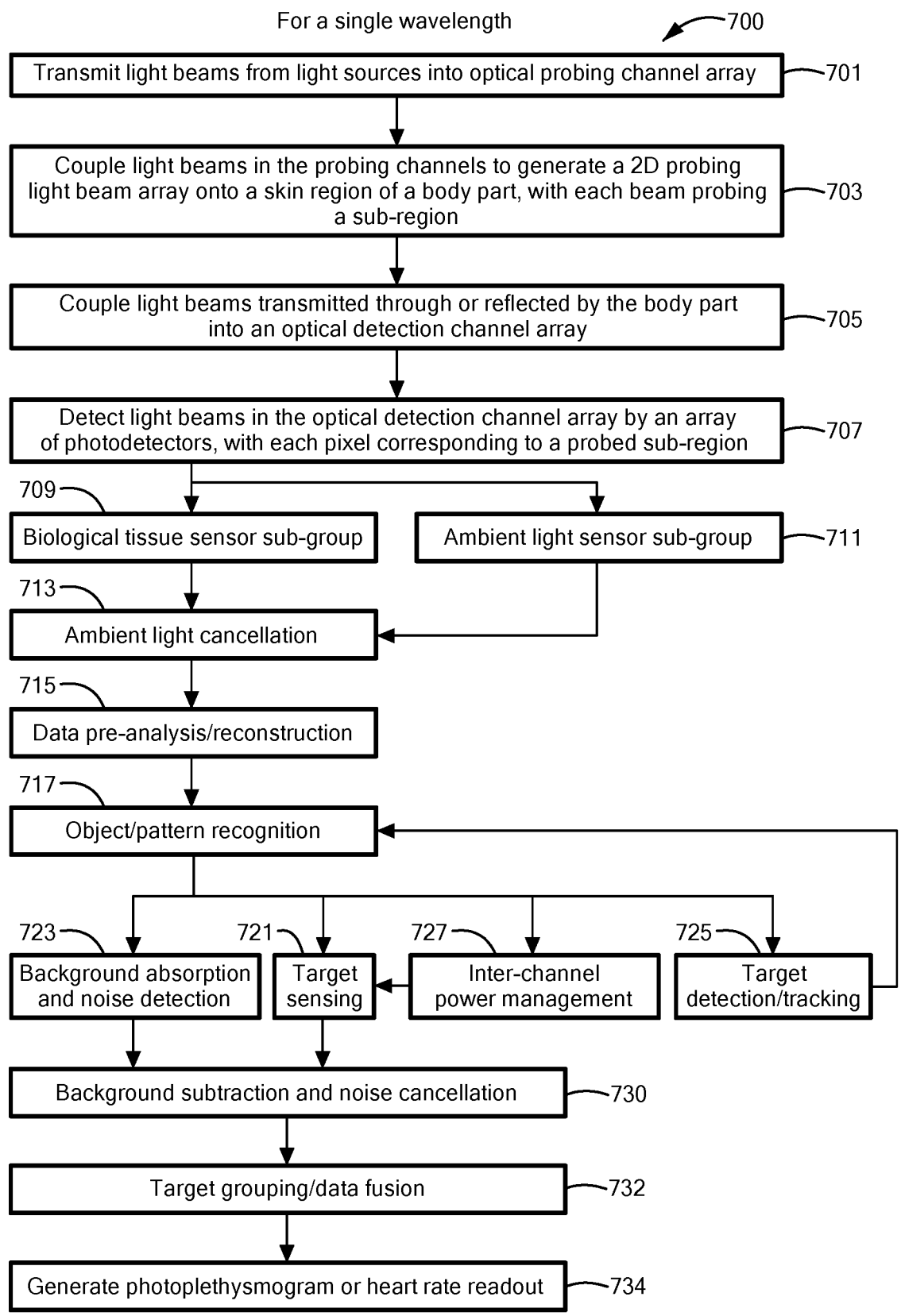
FIG. 7 is a flowchart depicting steps in a method for deriving targeted characteristics of a biological sample based on sorting data from subsets of sensing channels, in accordance with an embodiment of the present invention.

A method for bio-optical sensing 700 is now described with reference to FIG. 7. Light beams emitted by one or a plurality of light sources (e.g., micro-LED arrays) are first coupled and transmitted into an optical probing channel array 701. The light beams are coupled (703) by the optical probing channel array to generate a 2-D probing light beam array onto a skin region of a body part, with each beam probing a subregion. The optical couplers of the optical probing channel array are configured so that the probing light beam array possess a variety of focal length, beam properties and illumination patterns, which allows probing a variety of body tissues (e.g., different blood vessels, skin, fat, muscles, bones, etc.) with different sizes, properties and at different depth under the skin. The properties of the probing beams (e.g., intensity, phase, or polarization) are modulated as they transmitted through the body tissues by, e.g., absorption or by any other physical process entailed in light-matter interactions.

The modulated light beams (either transmitted through, scattered by, or reflected by, the body part) are subsequently captured (705) by an optical detection channel array, with each detection channel configured corresponding to a probing channel. The optical detection channel array then couple the modulated light beam array to a photodetector pixel array, with each photodetector pixel corresponding to a probed subregion (707). As a result, multiple optical sensing channels (each channel consisting of a light source, an optical probing channel, an optical detection channel, and a photodetector pixel) are created over the region of interest with each channel sensing a subregion. For some embodiments, there may be a one-to-many correspondence or many-to-one correspondence between the optical probing channels and optical detection channels. For example, for some optical paths that are highly scattering, a single optical channel may be used associated with an array of optical detection channels. In another example, a coherent light source or light source array is used and the light scattered by multiple subregions form an interference pattern that is collected by the detection waveguide array and directed to the photodetector pixel array.

The optical sensing channels can be assigned to different tasks/sub-groups. For example, while most of the channels are used for optical sensing of biological tissues (709), some sensing channels may be configured to detect (711) ambient light level that may vary due to, e.g., incident sunlight, indoor lighting, etc. After the ambient light intensity is measured, an ambient light cancellation step (713) is performed to remove such noises from the data captured by the bio-optical sensing channels.

The next step is pre-analysis and reconstruction (715) of data captured on each photodetector pixel of the bio-optical sensing system. As a depth-resolved 2-D transmission data matrix of the probed tissue region is created on the photodetector pixel array based on the transmitted beam properties, by comparing with known transmission properties, shapes, and patterns of target tissues (e.g., arterial or capillary blood vessels) and other tissues (e.g., fat, muscles, skin, bones, venous blood vessels, etc.) from a general database, a computer program is utilized to analyze the pixel array pattern and recognize (717) the composition of the biological tissues that a light beam transmits through. The data from each optical channel are combined and reconstructed to form a depth-resolved 2-D image of the probed tissue region, allowing the identification of tissue types, sizes, position, etc.

After a 2-D image of the region is obtained, depending on the tissue or zone probed, the optical sensing channel arrays are sorted and assigned for different tasks: main target sensing (721), background absorption (723) and noise detection, target tracking/detection (725), and inter-channel power management (727). Data collected from channels probing a background region nearby a target tissue (e.g., arterial or capillary vessels) is subtracted from data collected from channels identified as probing the target tissue to cancel (730) the background absorption and noises. Artifacts due to venous blood pulsation may also be subtracted. Such a pattern recognition approach can also track and keep sensing a tissue of interest even if the object has moved away from previous optical channels/pixels that cover this region. The 2-D image or key markers on the target tissue are continuously monitored to dynamically assign optical sensing channels to probe the target tissue and collect data onto the corresponding photodetector pixels. As a result, the optical sensing system's susceptibility to motion artifacts are dramatically reduced due to the multi-dimensional data collection scheme. The optical power launched from light sources (LEDs, for example) across the optical sensing channels are dynamically adjusted: for example, light sources or optical channels that illuminate regions not of interest to the current measurement are selectively turned off. The optical sensing system may also selectively increase or reduce optical power in one or several light sources or optical channels for regions of particular interest to improve the overall SNR.

For probed subregions that are identified as having the same composition of biological tissues but are not physically associated as one object (e.g., capillary bed tissues), their data are re-grouped and fused (732) to form high-SNR signals from multiple channels with low SNR. For example, PPG data collected from blood capillaries are typically considered less accurate than data collected through arteries and are easily compromised by the existence of other tissues. By analyzing the 2-D image of the probed-region and selecting subregions that are mostly dominated by capillary absorption, data retrieved from such channels are decoupled from other tissues and can be fused together and reconstructed to provide a more precise readout of the capillary-related absorption with enhanced SNR.

After the above-mentioned processes and a repeated analysis across different wavelengths, refined PPG signal or heart-rate readouts (734) are generated with a high fidelity, high SNR, immunity to motion artifacts, and low power consumption.

Although aspects of embodiments may be described with reference to flowcharts and/or block diagrams, functions, operations, decisions, etc. of all or a portion of each block, or a combination of blocks, may be combined, separated into separate operations or performed in other orders. All or a portion of each block, or a combination of blocks, may be implemented as computer program instructions (such as software), hardware (such as combinatorial logic, Application Specific Integrated Circuits (ASICs), Field-Programmable Gate Arrays (FPGAs) or other hardware), firmware or combinations thereof. Embodiments may be implemented by a processor executing, or controlled by, instructions stored in a memory. The memory may be random access memory (RAM), read-only memory (ROM), flash memory or any other memory, or combination thereof, suitable for storing control software or other instructions and data.

Instructions defining the functions of the present invention may be delivered to a processor in many forms, including, but not limited to, information permanently stored on tangible non-writable, non-transitory storage media (e.g., read-only memory devices within a computer, such as ROM, or devices readable by a computer I/O attachment, such as CD-ROM or DVD disks), information alterably stored on tangible writable, non-transitory storage media (e.g., floppy disks, removable flash memory and hard drives) or information conveyed to a computer through a communication medium, including wired or wireless computer networks. Moreover, while embodiments may be described in connection with various illustrative data structures, systems may be embodied using a variety of data structures.

The embodiments of the invention described above are intended to be merely exemplary; numerous variations and modifications will be apparent to those skilled in the art. All such variations and modifications are intended to be within the scope of the present invention as defined in any appended claims.

We claim:

1. A sensor for monitoring a characteristic of an organism, the sensor comprising:
   a. a plurality of light sources disposed upon a substrate and arranged in an array;
   b. for each of the plurality of light sources, a first waveguide for conveying light from the respective light source to a probed region of the organism, wherein light from at least two of the plurality of light sources is conveyed by their respective first waveguides to different respective subregions of the probed region;
   c. for each of the plurality of light sources, a second waveguide for collecting light from the respective light source after interaction with the probed region; and
   d. for each of the plurality of light sources, a detector pixel in an array of detector pixels for receiving light from a respective second waveguide and generating a corresponding pixel signal, the array of detector pixels thereby generating a plurality of pixel signals; and
   e. a processor for deriving a value of the characteristic of the organism based at least upon the plurality of pixel signals.

2. A sensor in accordance with claim 1, wherein the sensor is a non-invasive photoplethysmography sensor.

3. A sensor in accordance with claim 1, wherein the substrate is conformally deformable.

4. A sensor in accordance with claim 1, wherein light is guided from the plurality of light sources to the probed region at least in part by an array of free-space optical components.

5. A sensor in accordance with claim 1, wherein light is guided from one of the plurality of light sources by more than one waveguide.

6. A sensor in accordance with claim 1, wherein light is guided from the probed region to the array of detector pixels at least in part by an array of free space optical components.

7. A sensor in accordance with claim 1, further comprising a modulator for modulating a property of the light from at least one of the plurality of light sources.

8. A sensor in accordance with claim 7, wherein the property of the light modulated by the modulator is beam intensity, beam phase, or beam polarization.

9. A sensor in accordance with claim 1, wherein the plurality of light sources includes a plurality of LEDs, or a plurality of coherent light sources.

10. A sensor in accordance with claim 1, wherein each detector pixel of the array of detector pixels corresponds to a distinct subregion of the probed region or a distinct point of an interference pattern formed by scattered light from multiple subregions of the probed region.

11. A sensor in accordance with claim 1, wherein at least one of the first waveguides comprises an optical coupling structure for illuminating a subregion of the probed region.

12. A sensor in accordance with claim 1, wherein at least one of the second waveguides comprises an optical coupling structure for receiving light from a subregion of the probed region.

13. A sensor in accordance with claim 1, wherein each detector pixel of the array of detector pixels is associated with a specified depth within the probed region.

14. A method for non-invasively sensing a specified feature of a sample, the method comprising:
   a. generating light by means of a plurality of light sources disposed upon a substrate and arranged in an array;
   b. illuminating a probed region of the sample with light from the plurality of light sources via an array of first waveguides, wherein each light source in the plurality of light sources has a respective first waveguide, wherein light from at least two of the plurality of light sources is conveyed by their respective first waveguides to different respective subregions of the probed region;
   c. generating a plurality of detector signals based on light conveyed from the probed region to an array of detector pixels using a plurality of second waveguides, wherein each light source in the plurality of light sources has a respective second waveguide; and
   d. sensing the specified feature of the sample by processing the plurality of detector signals.

15. A method in accordance with claim 14, wherein sensing the specified feature includes (a) temporally resolving evolution of the plurality of detector signals, (b) discriminating between the specified feature and any background feature based on a specified spatial or temporal characteristic of the specified feature, (c) dynamically assigning distinct first waveguides to distinct monitored features of the sample, (d) binning data from a specified subset of detector pixels to enhance measurement accuracy or (e) analyzing the temporal and spatial variance of the speckle pattern formed by interference from scattered light.

16. A method in accordance with claim 14, wherein the specified feature includes a vital body sign.

17. A method in accordance with claim 14, wherein illuminating the probed region of the sample includes coupling light out of the array of first waveguides to generate an array of beams incident upon the sample or temporally modulating a property of the light from the plurality of light sources.

18. A method in accordance with claim 14, wherein each detector pixel of the array of detector pixels corresponds to a subregion of the probed region of the sample, corresponds uniquely to a subregion of the probed region of the sample, or corresponds to a point of a pattern formed by scattered light from multiple subregions of the probed region of the sample.

19. A method in accordance with claim 14, wherein illuminating the probed region of the sample includes coupling light out of the array of first waveguides in such a manner that light emerges from distinct first waveguides with a plurality of focal properties.

20. A method in accordance with claim 14, wherein generating light by means of the plurality of light sources includes selectively governing optical power output of distinct light sources of the plurality of light sources in order to selectively enhance signal from specified subregions of the probed region of the sample.

* * * * *